United States Patent
Chen et al.

(10) Patent No.: US 8,877,746 B2
(45) Date of Patent: Nov. 4, 2014

(54) COMPOSITIONS FOR DELIVERY OF INSOLUBLE AGENTS

(75) Inventors: Hailiang Chen, San Diego, CA (US); Andrew Xian Chen, San Diego, CA (US); Patricia Frech, Horgen (CH); Khawla Abu-Izza, Woburn, MA (US); Christoph Schmidt, Lausanne (CH)

(73) Assignee: Cardioklne, Inc, Cary, NC (US)

( * ) Notice: Subject to any disclaimer, the term of this patent is extended or adjusted under 35 U.S.C. 154(b) by 0 days.

(21) Appl. No.: 13/391,440

(22) PCT Filed: Aug. 24, 2010

(86) PCT No.: PCT/US2010/046452
§ 371 (c)(1),
(2), (4) Date: Sep. 21, 2012

(87) PCT Pub. No.: WO2011/025771
PCT Pub. Date: Mar. 3, 2011

(65) Prior Publication Data
US 2013/0079334 A1    Mar. 28, 2013

Related U.S. Application Data

(60) Provisional application No. 61/236,865, filed on Aug. 25, 2009.

(51) Int. Cl.
| | | |
|---|---|---|
| *A61K 31/55* | (2006.01) | |
| *A61K 31/355* | (2006.01) | |
| *A01N 43/62* | (2006.01) | |
| *A01N 43/16* | (2006.01) | |
| *A61K 47/22* | (2006.01) | |
| *A61K 31/5517* | (2006.01) | |

(52) U.S. Cl.
CPC ............. *A61K 47/22* (2013.01); *A61K 31/5517* (2013.01)
USPC ........................... 514/220; 514/449; 514/458

(58) Field of Classification Search
USPC .......................................... 514/220, 449, 458
See application file for complete search history.

(56) References Cited

U.S. PATENT DOCUMENTS

| | | |
|---|---|---|
| 6,352,718 B1 | 3/2002 | Yoon et al. |
| 2003/0069227 A1 | 4/2003 | Ellis-Grosse et al. |
| 2006/0003002 A1 | 1/2006 | Fikstad et al. |
| 2006/0024360 A1 | 2/2006 | Chen |
| 2007/0104778 A1 | 5/2007 | Zeng et al. |
| 2007/0116729 A1 | 5/2007 | Palepu |
| 2007/0207173 A1 | 9/2007 | Chen |
| 2007/0218012 A1 | 9/2007 | Bittorf et al. |
| 2008/0027052 A1 | 1/2008 | Moe et al. |
| 2008/0221084 A1 | 9/2008 | Liu et al. |

OTHER PUBLICATIONS

International Preliminary Report on Patentability, issued in PCT/US2010/046452, dated Mar. 8, 2012.
International Search Report, issued in PCT/US2010/046452, dated Oct. 5, 2010.

*Primary Examiner* — My-Chau T Tran
(74) *Attorney, Agent, or Firm* — Brinks Gilson & Lione

(57) ABSTRACT

Compositions and methods of making the same for in vivo delivery of lixivaptan to a subject in need thereof are described. The composition includes a substantially water-insoluble pharmacologically active agent (e.g., lixivaptan) and a substantially water-insoluble matrix forming material (e.g., a Vitamin E semi-ester), wherein the pharmacologically active agent is dispersed in said matrix forming material, and wherein the composition delivers said substantially water-insoluble pharmacologically active agent upon exposure to physiological medium.

22 Claims, 5 Drawing Sheets

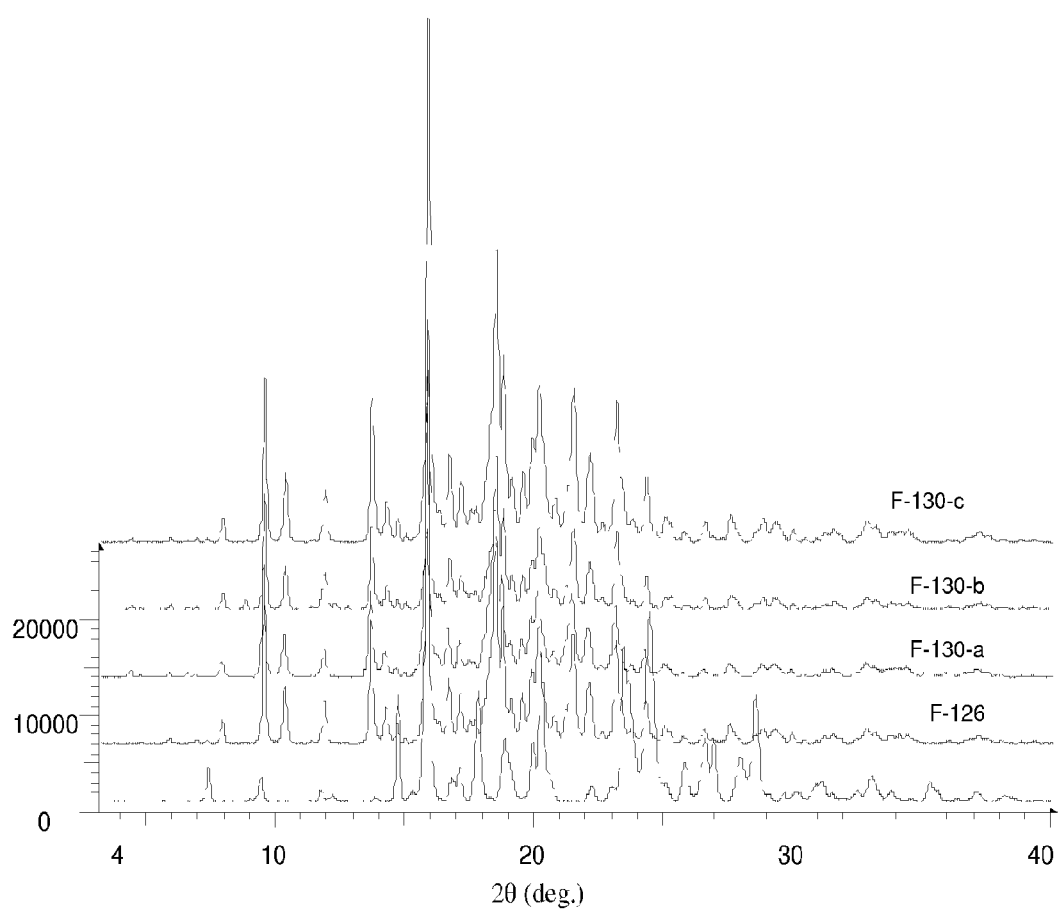

FIG. 3A
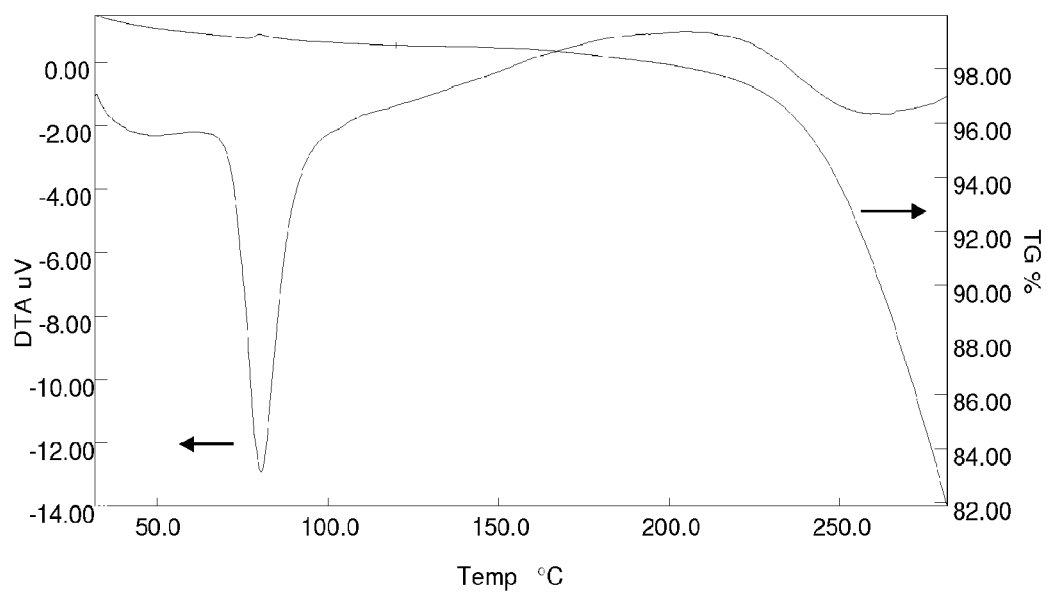
FIG. 3B
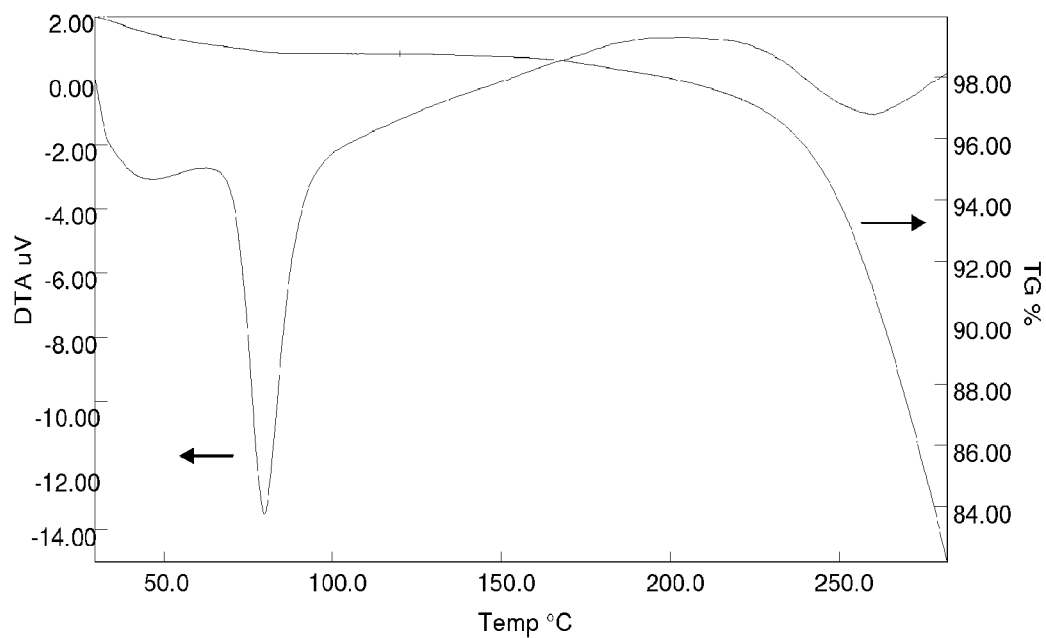
FIG. 4

COMPOSITIONS FOR DELIVERY OF INSOLUBLE AGENTS

This application is a National Stage application of International Application No. PCT/US2010/046452, filed Aug. 24, 2010, which claims the benefit of U.S. Provisional Application No. 61/236,865, filed Aug. 25, 2009, the entire contents of which are hereby incorporated herein by reference.

CLAIM OF PRIORITY

This application claims priority to provisional U.S. Patent Application No. 61/236,865, filed Aug. 25, 2009, which is incorporated by reference in its entirety.

TECHNICAL FIELD

The invention relates to compositions for delivery of substantially water-insoluble pharmacologically active agents, methods of making same and methods of delivery employing same.

BACKGROUND

Insoluble pharmacologically active agents, e.g., itraconazole, progesterone, cyclosporin, carbamazepine, fenofibrate, amphotericin B, naproxen, and glyburide, present oral absorption challenges due to their low solubility in aqueous medium. According to the Noyes-Whitney equation (Alfred Martin et al., Physical Pharmacy, $3^{rd}$ ed, page 575), drug dissolution rate is directly proportional to its solubility, and hence an insoluble drug is intrinsically of slow dissolution. Many insoluble pharmacologically active agents are present in crystalline form that can be an additional energy barrier to drug dissolution.

As the pharmacologically active agent (e.g., drug) moves through the human gastrointestinal tract after oral administration, its typical residence time in the stomach, intestines and colon is about 30 minutes, 3 hours and 30 hours, respectively. The pharmacologically active agent must dissolve in these time windows to allow for absorption. A pharmacologically active agent with a slow rate of dissolution, i.e., a significant portion of the agent fails to dissolve during its transit through the gastrointestinal tract, will simply not be entirely absorbed.

It is well understood that slow dissolution is a major reason for lack of oral absorption of insoluble pharmacologically active agents, and can cause an otherwise promising drug candidate compound to fail further drug development. Slow dissolution is also frequently related to high absorption variability among patients, high food effect on absorption and lack of dose-exposure relationship. Each of these can contribute to suboptimal drug performance. It is estimated that 40-60% of discovered drug substances are insoluble and many of them suffer from the oral absorption problem.

Several approaches have been developed to improve solubility and/or dissolution rate of insoluble pharmacologically active agents. Common approaches include: converting an insoluble pharmacologically active agent into a more soluble salt or crystalline form including amorphous form; reducing the particle size of an insoluble pharmacologically active agent for faster dissolution; dissolving an insoluble pharmacologically active agent in a liquid medium comprising water-soluble components such as solvents and surfactants, etc., to form a "liquid formulation" (such as, for example, an emulsion); and dissolving or dispersing an insoluble pharmacologically active agent in a solid matrix comprising water-soluble or hydrophilic components, such as a solid polymer or lipids, to form a "solid dispersion formulation".

The above approaches have been applied in preparing or formulating some successful drug products. Insoluble naproxen was made soluble by forming a sodium salt, which is the active ingredient of the drug Naprosyn®. Size reduction by micronization has lead to drugs Prometrium® (micronized progesterone) and Micronase® (micronized glyburide). Dissolving the drug in a water-soluble liquid composition was the basis for drugs such as Sandimmune® (cyclosporin emulsion) and Neoral® (cyclosporin microemulsion). Dispersion of the insoluble griseofulvin in a solid dispersion matrix comprising water-soluble polymer propylene glycol (PEG) resulted in the drug Gris-PEG®.

The above approaches are based on the physical chemistry theories of drug solubility and dissolution. For example, a salt or an amorphous form of a pharmacologically active agent is commonly known to be more soluble and of faster dissolution than the unmodified pharmacologically active agent itself. Particle size reduction generates a greater surface area and a greater surface area leads to a faster dissolution rate as predicted by the Noyes-Whitney equation (Alfred Martin et al, Physical Pharmacy, $3^{rd}$ ed, page 575). The liquid formulation first breaks up the crystals of the pharmacologically active agent by dissolving it in a water-soluble solvent and such water-liking solution can then readily be mixed into another aqueous environment such as gastric fluid, carrying the dissolved pharmacologically active agent to achieve a fast dissolution. Similarly, in a solid dispersion formulation, the insoluble pharmacologically active agent is also first dissolved or dispersed in a solid matrix formed with a soluble ingredient, e.g. PEG or PVP, the matrix can then be readily mixed into the aqueous biological milieu providing a fast dissolution of the dissolved pharmacologically active agent, owing to the hydrophilic nature of the matrix-forming ingredient.

In essence, the liquid formulation and solid dispersion formulation are based on the same principle, i.e., (1) to dissolve the insoluble pharmacologically active agent in a water-soluble or hydrophilic matrix (liquid or solid) first to break the crystalline structure of the pharmacologically active agent, and (2) to render a fast mixing of the water-liking matrix with a biological aqueous milieu (gastric or intestinal fluid) with the already dissolved or dispersed pharmacologically active agent in it to allow for a fast dissolution.

In practice, these approaches suffer from several disadvantages. Some insoluble pharmacologically active agents cannot be converted to the more soluble salts or crystalline form, especially those that lack ionizable groups. Particle size reduction by micronization or nanonization presents processing and stability challenges, as well as dissolution limitations, since the micronized or nanosized pharmacologically active agent may still possess a high degree of crystallinity. Liquid formulations present drug precipitation and packaging challenges, due to solvent evaporation. Moreover, non-solid formulations are more prone to chemical instability and capsule-shell incompatibility, leading to the possibility of leakage upon storage. Solid dispersion formulations often suffer from re-crystallization of the insoluble pharmacologically active agent over time, resulting in decreased dissolution.

SUMMARY

A substantially water-insoluble pharmacologically active agent can be made fast dissolving and/or imparted with improved bioavailability by employing a substantially water-insoluble matrix forming material instead of the water-soluble matrix materials used in conventional methods, which would seem counter-intuitive. Nevertheless, surprisingly enhanced dissolution and oral absorption of substantially water-insoluble pharmacologically active agents have been demonstrated to provide significantly broad utility.

For clarification, the compositions are not directed to a slowrelease formulation. Unlike formulations where water-insoluble matrix forming materials are used to slow down the dissolution of certain drugs, compositions and methods described here are for achieving fast dissolution of substantially water-insoluble pharmacologically active agents. Moreover, compositions described herein are not directed to water-soluble pharmacologically active agents, for which dissolution enhancement is not typically needed.

In one aspect, a pharmaceutical composition includes a single oral dosage form including an oil-free and substantially water-free solid dispersion, the dispersion including a therapeutically effective amount of lixivaptan and 50% or more by weight of a vitamin E semi-ester, such as vitamin E succinate (VES).

In one aspect, the composition can further include a surfactant. The surfactant is an alkyl sulfate salt, such as for example, sodium lauryl sulfate. The dispersion can be substantially free of crystalline lixivaptan, and can include 60% or more, 70% or more, or 80% or more by weight of the vitamin E semi-ester. In still another aspect, the composition further includes a disintegrant. The disintegrant can be a crosslinked poly(vinylpyrrolidone), and the composition can further include a polymer or a plant protein, such as for example, zein.

In another aspect, a method of making a pharmaceutical composition includes dissolving an amount of lixivaptan in a non-aqueous solvent, dissolving an amount of a vitamin E semi-ester in the non-aqueous solvent, and removing the solvent, thereby forming a solid dispersion including lixivaptan and the vitamin E semi-ester. In this aspect, the dispersion is substantially free of crystalline lixivaptan.

In one aspect, the method includes mixing the solid dispersion with a disintegrant. The method also can include mixing the solid dispersion with a surfactant. In another aspect, the method includes dissolving an amount of a water-soluble protein in the non-aqueous solvent, and removing the solvent by spray drying.

The details of one or more embodiments are set forth in the accompanying drawings and description below. Other features, objects, and advantages will be apparent from the description and drawings.

BRIEF DESCRIPTION OF THE FIGURES

FIG. 2 displays X-ray powder diffraction spectra for samples of lixivaptan and lixivaptan formulations.

FIGS. 3A-3B present TGA and DSC results of lixivaptan formulations following exposure to storage conditions.

DETAILED DESCRIPTION

Figure 1A:
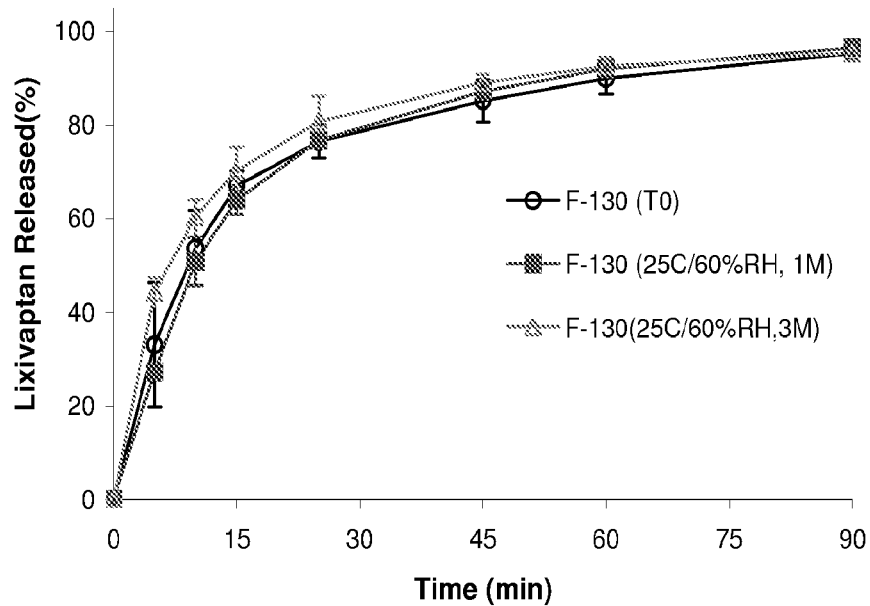
FIGS. 1A-1B illustrate dissolution profiles of lixivaptan formulations following exposure to storage conditions.

Solid dispersion formulations sometimes are called by different names depending upon their preparation processes. For example, a solid dispersion may be referred to as a "hot melt" formulation, if it is prepared by first dissolving the pharmacologically active agent in a molten polymer or lipid, and then cooling molten solution to form a semi-solid matrix. Water-soluble surfactants, e.g. vitamin E TPGS, or water-soluble or hydrophilic polymer, e.g. polyethylene glycol (PEG) of low melting point (<60 deg C.) or mixture thereof, are commonly used in a hot melt formulation.

In other cases, a solid dispersion is called a "spray-dried amorphous formulation" when prepared by first dissolving a pharmacologically active agent and a water-soluble or hydrophilic polymer, e.g. polyvinyl pyrrolidone or HPMC in a solvent (ethanol etc.), and then spray drying the solution to obtain a solid dispersion. Alternatively, a solid dispersion is prepared by dissolving the pharmacologically active agent in a molten lipid or polymer and then spray-congealing to form particles. Despite the difference in their preparation process or names, solid dispersion formulations share the same composition features, i.e. an insoluble pharmacologically active agent dissolved or dispersed in a matrix formed by water-soluble ingredients, and the same concept of enhancing dissolution, i.e., an insoluble pharmacologically active agent is made fast dissolving by using a water-soluble or hydrophilic matrix-forming ingredient.

Although there was a great interest in solid dispersion systems during the past four decades as a means of increasing the dissolution rate and bioavailability of poorly water-soluble pharmacologically active agents, their commercial application has been very limited, primarily because of problems with manufacturing and drug stability. Solid dispersions of pharmacologically active agents were generally produced by the hot melt method. The materials, which were usually semisolid, were hardened by cooling. They were then pulverized, sieved, mixed with relatively large amounts of excipients, and encapsulated into hard gelatin capsules or compressed into tablets. These operations were difficult to scale up for the manufacture of dosage forms. A solid dispersion formulation suffers from potential degradation of the pharmacologically active agent in the hot melt process, and a lack of free-flowing property prevents encapsulation or tablet compression using conventional capsule fillers or a tablet press. In addition, a "solid dispersion" or a "hot melt" is almost exclusively prepared using a synthetic polymer such as PEG, polyvinyl pyrrolidone (PVP), or polyvinyl pyrrolidone vinyl acetate copolymer (PVPVA) that melts at a temperature below 150° C. Due to its safety limitations, the amount of such a polymer that can be dosed orally to a human subject can be very limited, thereby preventing its use in a product designated for human consumption, especially, for chronic use.

As used herein, the term "water-insoluble" refers to the limited solubility of a pharmacologically active agent in aqueous solutions (such as water, physiological saline, injectable dextrose solutions, etc). The United States Pharmacoepia/National Formulary (USP/NF) generally expresses solubility in terms of the volume of solvent required to dissolve 1 gram of the pharmacologically active agent at a specified temperature (e.g., 1 g aspirin in 300 mL water or 5 mL ethanol at 25° C.). Other references may use more subjective terms to describe solubility, such as those given in the following table from *Remington's Pharmaceutical Sciences*, Mack Publishing Co., Easton, Pa., by Joseph Remington and Alfonso Gennaro: Mack Publishing, 1995,

TABLE 1

| Descriptive terms | Parts of solvent needed for 1 part solute |
|---|---|
| Very soluble | <1 |
| Freely soluble | 1-10 |
| Soluble | 10-30 |
| Sparingly soluble | 30-100 |
| Slightly soluble | 100-1000 |

TABLE 1-continued

| Descriptive terms | Parts of solvent needed for 1 part solute |
|---|---|
| Very slightly soluble | 1000-10,000 |
| Practically insoluble or insoluble | >10,000 |

Thus, as used herein, "water-insoluble pharmacologically active agents" include the pharmacologically active agents in the last four solubility categories, i.e., "sparingly soluble," "slightly soluble," "very slightly soluble," and "practically insoluble or insoluble," when water is used as the solvent. Thus, the phrase "substantially water-insoluble active agents" means those agents that are sparingly, slightly, or very slightly soluble, or practically insoluble according to the definitions for solubility provided in Table 1 above.

As used herein, the term "water-insoluble" may be used interchangeably with hydrophobic, lipophilic, oleophilic, and similar terms.

As used herein, the term "substantially water-insoluble matrix forming materials" refers to substantially water insoluble solid materials that are capable of forming solid particles or granules that preferably are dry, non-sticky, free flowing, and/or non-hygroscopic, especially when such materials contain substantially water-insoluble pharmacologically active agents dispersed therein. Substantially water insoluble solid materials can have a solubility of, for example, less than 1.0 g/100 g water, less than 0.1 g/100 g water, less than 0.01 g/100 g water, less than 0.001 g/100 g, or less than 0.0001 g/100 g water. When dispersed in a substantially water-insoluble matrix forming material, it is preferred that the pharmacologically active agents exist in a substantially amorphous form or are free of their original crystalline forms as determined by suitable methods, which can include, e.g., differential scanning calorimetry (DSC), differential thermal analyzer (DTA) or X-ray powder diffraction (XRPD). As used herein, the term "substantially water-insoluble matrix forming materials" does not include any water-soluble liquid or semi-solid material, specifically, materials such as PEG, PVP, HPMC, HPC, cremophor, gelucire, vitamin E TPGS, water-soluble waxes, surfactants, or water soluble excipients, salts, or additives thereof.

The preferred substantially water-insoluble matrix forming materials comprise water-insoluble nutrient(s). As used herein, the term "nutrient(s)" refers to ingredients that are derived from a natural source found in human diet and digestible by the human digestive system to provide nutritional benefit, i.e. enzymatically digestable. The nutrients contemplated for use herein are traditionally used as food additives, nutritional supplements or as a pharmaceutical ingredient for purposes other than a pharmacologically active agent or a matrix forming material. Surprisingly, These insoluble nutrients enhance dissolution and increase oral absorption of the substantially water-insoluble pharmacologically active agents.

Without being bound by any theory or mechanism, it is proposed that the water-insoluble nutrients provide improved dissolution and oral absorption for substantially water-insoluble pharmacologically active agents by one or more of the following mechanisms:

Initially, a substantially water-insoluble pharmacologically active agent is dispersed in a substantially water-insoluble matrix forming material (e.g. nutrient) according to the process described herein, wherein the substantially water-insoluble pharmacologically active agent exists in an amorphous, partially crystalline, or crystalline form that is more energetically favorable for dissolution, once the surrounding matrix is removed.

When exposed to an aqueous milieu (e.g., gastrointestinal fluid), the water-insoluble matrix, due to its insoluble nature, continues to hold the pharmacologically active agent in the matrix. This prevents the pharmacologically active agent from being immediately released ("dumped") into the aqueous milieu. An immediate release is not desirable because it can lead to a rapid increase in concentration that exceeds the solubility in the aqueous milieu, which in turn can lead to rapid precipitation of the pharmacologically active agent before it reaches its potential absorption site, e.g., in the intestines. Such premature drug release is common with other approaches where an insoluble drug in a very water-soluble matrix is released immediately upon exposure to an aqueous milieu.

The water-insoluble matrix as described herein may be designed to release the drug only when an additional locally released external factor is present. The locally released external factor can be for example, a gastrointestinal enzyme that digests the water-insoluble digestible matrix, or a bile salt or a surfactant that dissolves the water-insoluble matrix. The matrix can include a nutrient chosen to be digested or dissolved by a desired external factor This localized enzyme- or bile-induced release allows the matrix particles to first reach the absorption sites prior to releasing the trapped pharmacologically active agents, which would occur at a rate similar to the natural digestion/absorption rate of the nutrients.

In a specific embodiment, the substantially water-insoluble matrix-forming materials are solid, insoluble and enzymatically digestable nutrients comprising proteins, peptides, amino acids, carbohydrates, lipids, phospholipds, vitamins, coenzymes or combinations thereof.

In another embodiment, the matrix forming materials are solid, substantially water-insoluble and enzymatically digestable or bile-soluble materials comprising synthetic polymers and naturally occurring celluloses, excluding the enteric-coating polymers, e.g., polymethacrylate or phthalate An enteric-coating polymer is water soluble at a neutral pH.

In a yet another specific embodiment, the substantially water-insoluble matrix-forming materials are solid, substantially water-insoluble and digestable plant proteins, milk proteins and animal proteins.

In a preferred embodiment, the substantially water-insoluble matrix-forming materials are zein, casein, whey, collagen, gelatin, insoluble amino acid, protein hydrolysates, or combinations thereof.

In another preferred embodiment, the substantially water-insoluble matrix-forming material includes a vitamin E derivative, such as, for example, a vitamin E semi-ester derivative where "vitamin E" refers to tocopherols, tocotrienols, and mixtures thereof. Tocopherols are a class of chemical compounds of various methylated phenols of which many have vitamin E activity. Tocotrienols are a related class of compounds, differing by unsaturation in the isoprenoid tail. Tocopherols and tocotrienols include alpha, beta, gamma and delta analogs (Scheme 1).

Scheme 1. Chemical structure of tocopherols and tocotrienols

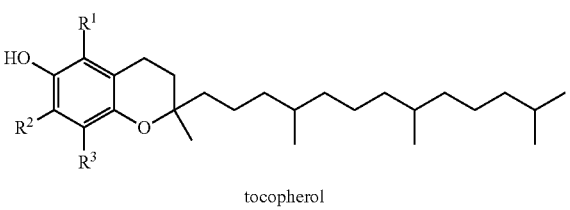

tocopherol

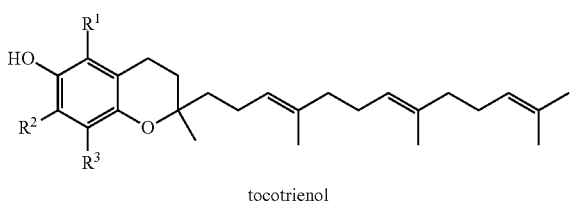

tocotrienol

| Designation | $R_1$ | $R_2$ | $R_3$ |
|---|---|---|---|
| Alpha | $CH_3$ | $CH_3$ | $CH_3$ |
| Beta | $CH_3$ | H | $CH_3$ |
| Gamma | H | $CH_3$ | $CH_3$ |
| Delta | H | H | $CH_3$ |

A tocopherol semi-ester derivative is given by the general formula I,

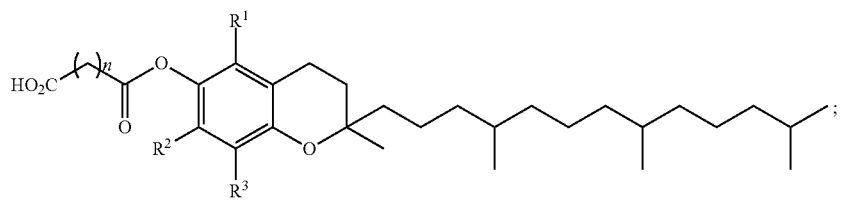

(I)

or a tocotrienol semi-ester derivative of the general formula II,

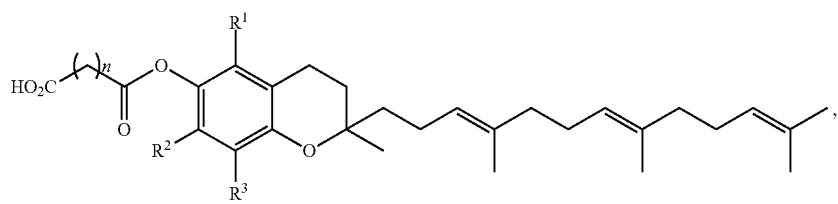

(II)

wherein $R^1$, $R^2$, and $R^3$ are each, independently, —H or —$CH_3$, and n is an integer in the range of 0 to 7.

As used herein, the term "vitamin E semi-ester" includes vitamin E derivatives that are hemi-esters of short-chain dicarboxylic acids with alpha tocopherol (or other tocopherols or tocotrienols), wherein the dicarboxylic acids have the general type formula:

HOOC—$(CH_2)_n$—COOH

Short-chain dicarboxylic acids comprise oxalic acid (n=0), malonic acid (n=1), succinic acid (n=2), glutaric acid (n=3), adipic acid (n=4), pimelic acid (n=5), suberic acid (n=6) and azelaic acid (n=7) acids (Scheme 2).

Scheme 2: alpha-tocopherol semi-ester derivatives:

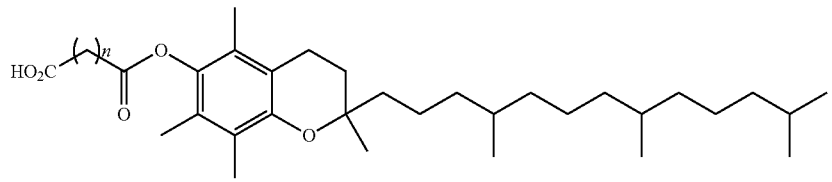

| Designation | n | Dicarboxylic acid |
| --- | --- | --- |
| Alpha-tocopheryl oxalate | 0 | Oxalic acid |
| Alpha-tocopheryl malonate | 1 | Malonic acid |
| Alpha-tocopheryl succinate | 2 | Succinic acid |
| Alpha-tocopheryl glutarate | 3 | Glutaric acid |
| Alpha-tocopheryl adipate | 4 | Adipic acid |
| Alpha-tocopheryl pimelate | 5 | Pimelic acid |
| Alpha-tocopheryl suberate | 6 | Suberic acid |
| Alpha-tocopheryl azelate | 7 | Azelaic acid |

The chemical name of racemic alpha tocopherol is (±)-2,5,7,8-tetramethyl-2-(4',8',12'-trimethyltridecyl)-6-chromanol (CAS Registry Number, 10191-41-0). It contains three chiral centers giving rise to eight isomers. The naturally occurring d-isomeric form represents the (2R,4'R,8'R)-alpha-tocopherol or RRR-alpha-tocopherol.

As used herein, the alpha-tocopheryl succinate preferably is d-alpha-tocopheryl acid succinate (CAS number 4345-03-3). The alpha-tocopheryl succinate may optionally comprise isomers such as dl-alpha-tocopheryl acid succinate. It may further comprise beta tocopheryl acid succinate, delta tocopheryl acid succinate, gamma tocopheryl acid succinate, alpha-tocotrienyl succinate, beta-tocotrienyl succinate, gamma-tocotrienyl succinate, delta-tocotrienyl succinate, or isomers thereof. The terms vitamin E succinate (VES) or alpha-tocopheryl succinate (ATS) refer to d-alpha-tocopheryl acid succinate and are used interchangeably.

As used herein, the "salts" of alpha-tocopherol semi-ester derivatives comprise ionic salts of pharmaceutically acceptable inorganic counter ions such as sodium, potassium, lithium, calcium, magnesium, aluminum, or the like as well as organic counter ions such as amines, lysine, arginine, or the like.

In certain embodiments, the vitamin E semiester used as the substantially water-insoluble matrix forming material comprises alpha-tocopheryl succinate, its salts or solvate.

All of the above tocopherol derivatives including alpha-tocopheryl succinate with vitamin activity may correctly be referred to as "vitamin E." The most common form of "vitamin E" used as an antioxidant and as a dietary supplement for vitamin E deficiency are tocopherol and tocopheryl acetate. Vitamin E TPGS (tocopherol polyetheleneglycol succinate) is used primarily as a surfactant in oral and parenteral drug formulations as a solubilizer or emulsifier.

Alpha-tocopherol semi-ester derivatives are structurally and functionally different from the other three common types of vitamin E derivatives, i.e., tocopherol, tocopherol monoester (e.g., acetate), and tocopherol polyetheleneglycol succinate (also referred to as tocopherol PEG ester or vitamin E TPGS). The semi-esters contain an open (non-esterified) carboxylic acid group and are ionizable, whereas all the other forms of vitamin E are non-ionizable. Thus, when included as a component in a formulation, the semi-esters behave differently from the monoesters or the parent tocopherol. While a monoester or the parent tocopherol is lipophilic and oil soluble, the semi-esters are not soluble in either water or oil, and so are poor solvents for either hydrophilic or hydrophobic pharmacologically active agents. By appearance, alpha-tocopheryl succinate is a crystalline, water-insoluble solid with a melting point of 75° C., whereas tocopherol and tocopherol acetate are oily liquids, and vitamin E TPGS is water-soluble semi-solid with a melting point of about 50° C. For clarification, tocopherol, tocopherol monoester (e.g., acetate) and vitamin E TPGS are not embraced by the term "substantially water-insoluble matrix forming materials."

In another embodiment, the substantially water-insoluble matrix forming material comprises in the range of 10% to 95% by weight of the matrix composition; preferably to be within the range of 25% to 90%, and more preferably to be at about 50% to 80% by weight.

In another embodiment, the substantially water-insoluble matrix forming material comprises alpha-tocopheryl succinate in combination with povidone at a weight concentration of no more than 25%.

In yet another embodiment, the compositions provide improved bioavailability of the substantially water-insoluble pharmacologically active agent relative to said pharmacologically active agent in the absence of said matrix forming material.

In yet another embodiment, the compositions exhibit faster dissolution in aqueous medium, relative to the water-insoluble pharmacologically active agent in the absence of said matrix forming material.

In certain embodiments, a composition includes (1) a substantially water-insoluble pharmacologically active agent and (2) alpha-tocopheryl succinate, wherein the compositions improve the bioavailability of said substantially water-insoluble pharmacologically active agent, and wherein said compositions are in the form of free-flowing, compressible and non-hydroscopic powder.

In another embodiment, a composition includes (1) a substantially water-insoluble pharmacologically active agent and (2) alpha-tocopheryl succinate, wherein the pharmacologically active agent exhibits faster dissolution as compared to the unmodified pharmacologically active agent and the total matrix-forming ingredient is in a range of 20% to 95% by weight of the solid composition.

As used herein, the term "powdered, free-flowing solid" or "dry free-flowing solid particles" refers to solid mass of small particles capable to passing through a standard 10 mesh sieve (2 mm) having a free-flowing property as defined by an angle of repose of less than 60 degrees. When bulk solid materials are poured onto a horizontal surface, a conical pile will form. The internal angle between the surface of the pile and the horizontal surface is known as the "angle of repose" and is related to the density, surface area, and coefficient of friction of the material. Material with a low angle of repose forms flatter piles than material with a high angle of repose. In other words, the angle of repose is the angle a pile forms with the ground.

As used herein, the term "amorphous" refers to a state in which the material devoid long range order of the positions of the atoms and, depending upon temperature, may exhibit the physical properties of a solid or a liquid (e.g. free flowing). Typically such materials do not give distinctive X-ray diffraction patterns, and lack a distinct melting event when examined by differential scanning calorimetry (DSC). It can be difficult to make a distinction between truly amorphous solids and crystalline solids if the size of the crystals is very small. Even amorphous materials have some short-range order at the atomic length scale due the nature of chemical bonding. Thus, the pharmacologically active agents in the matrix may be about 50%, 60%, 70%, 80%, 90%, 95%, 99%, 99.9%, or 99.99% or more amorphous by weight.

As used herein, the term "dissolution" refers to a process of dissolving a solid substance into a solvent to yield a solution. In pharmaceutical practices, dissolution usually refers to the rate, kinetics and extent to which the pharmacologically active agent dissolves from its dosage form into a selected dissolution medium in a test vessel (in vitro dissolution) or into a biological milieu such as gastric fluid in the body (in vivo dissolution). Dissolution refers to the in vitro dissolution rate of the pharmacologically active agent in a typical in vitro dissolution medium, such as water, water with some surfactant, simulated gastric fluid, USP or simulated intestinal fluid, USP, tested by a standard USP dissolution apparatus (Type 1 or Type 2). It is generally agreed that a fast and complete in vitro dissolution is indicative of better absorption of the pharmacologically active agent in vivo.

The compositions can optionally be combined with one or more additives, sometimes referred to as excipients. The excipients that can be combined to improve or control the tableting or encapsulation or dissolution property of powdered, free-flowing amorphous pharmaceutical compositions may include, but are not limited to (1) binders, (2) bulking agents, (3) wetting agents, (4) disintegrants, (5) sustained release matrix forming agents, (6) lubricants or glidants, (7) antioxidants, (8) buffer, (9) colorants or flavorants, (10) coating agents. Alternatively, the additives can be contained in the pharmaceutical composition. The functions and selection of these additives are well known in the art, and are further described in such references as Pharmaceutical Dosage Forms: Tablets, Vol. 1-3, by Herbert Lieberman et al., which is incorporated by reference in its entirety.

In another embodiment, there are provided methods for delivery of a substantially water-insoluble pharmacologically active agent to a subject in need thereof, said methods comprising administering to said subject an effective amount of a composition.

In yet another embodiment, there are provided fast dissolving particles comprising substantially water-insoluble pharmacologically active agents dispersed in a substantially water-insoluble matrix wherein said fast dissolving particle is in the form of a free-flowing, compressible and non-hydroscopic powder.

There are also provided processes for preparing a solid matrix comprising a substantially water-insoluble pharmacologically active agent or salt or solvate thereof, dispersed in a substantially water-insoluble matrix-forming material. The process includes: (a) dissolving the substantially water-insoluble pharmacologically active agent or salt or solvate thereof and the substantially water-insoluble matrix-forming material therefor in one or more solvents; and (b) removing solvent(s) under suitable conditions. In certain embodiments, step (b) is carried out by suitable means, such as vacuum drying, air drying or spray drying. In other embodiments, step (b) is carried out to form particles of size in the range of about 1 µm to about 1 mm in diameter. In another embodiment, the processes further comprise pulverizing, ball-milling, comminuting or jet milling to form a free-flowing, compressible and non-hydroscopic powder.

In a certain embodiment, the process for preparing a composition for in vivo delivery of a substantially water-insoluble pharmacologically active agent to a subject in need thereof includes: (a) dissolving the substantially water-insoluble pharmacologically active agent or salt or solvate thereof and a substantially water-insoluble matrix forming material in at least one or more solvents; and (b) removing said solvent(s) under suitable conditions. In certain embodiments, step (b) is carried out by suitable means, such as vacuum drying, air drying or spray drying. In other embodiments, step (b) is carried out to form particles of size in the range of about 1 µm to about 1 mm in diameter. In another embodiment, the processes further comprise pulverizing, ball-milling, comminuting or jet milling to form a free-flowing, compressible and non-hydroscopic powder.

In general, the compositions are prepared by (1) co-dissolution, (2) drying, and (3) comminution. The co-dissolution is the dissolution of the substantially water-insoluble pharmacologically active agent and the substantially water-insoluble matrix forming material, e.g., vitamin E succinate, in a volatile solvent or mixture of volatile solvents to form a solution. A volatile solvent refers to a solvent that can be removed by a common drying method. The volatile solvent may include water and pharmaceutical solvents such as those defined by the FDA as Class 3 and Class 2 solvents (FDA's Guidance for Industry, Q3C, which is incorporated by reference in its entirety). Examples of Class 3 solvents, which are the most preferred, are as follows:

TABLE 2

| Class 3 Solvents Which Should Be Limited by GMP or Other Quality-Based Requirements |
|---|
| Acetic acid |
| Acetone |
| Anisole |
| 1-Butanol |
| 2-Butanol |
| Butyl acetate |
| tert-Butylmethyl ether |
| Cumene |
| Dimethyl sulfoxide |
| Ethanol |
| Ethyl acetate |
| Ethyl ether |
| Ethyl formate |
| Formic acid |
| Heptane |
| Isobutyl acetate |
| Isopropyl acetate |
| Methyl acetate |
| 3-Methyl-1-butanol |
| Methylethyl ketone |
| Methylisobutyl ketone |
| 2-Methyl-1-propanol |
| Pentane |
| 1-Pentanol |
| 1-Propanol |
| 2-Propanol |
| Propyl acetate |

The solution of the pharmacologically active agent and the matrix forming material in a volatile solvent is subsequently reduced to remove the solvent and to produce a dry solid mass. The drying method may include vacuum drying, rotary drying, drum drying, spray drying, freeze-drying, lyophilization, drug layering, spray granulation, or other drying method. Drug layering involves spraying the solution onto inert cores (e.g., sugar spheres or microcrystalline cellulose spheres) and directly filling into capsules or compression into tablets, avoiding a milling step. Spray granulation involves spraying the solution onto a powder of inert pharmaceutical excipients to form a granulation, which is then filled into capsules or compressed into tablets, avoiding a milling step. The residual level of the solvent in the dry mass is preferably less than 10%, more preferably less than 5% and most preferably less than 1%.

The dried solid mass can be further reduced in size by a comminution method to produce a powdered, free-flowing amorphous pharmaceutical composition. Comminution refers to process to reduce particle size of solids. Machines used for comminution may include jaw crusher, cone and gyratory crushers, roller crusher, impact crusher, tube mills, ball mills, autogenous mills, vertical roller mills, and roller presses. Common comminutors found in the field include ball mill, Fitzmill, and Quadro Comil, etc. The comminution may include a sieving step at the end to control the particle size of the powdered, free-flowing amorphous pharmaceutical compositions.

Some compositions are suitable for manufacture by melt granulation or hot melt extrusion. Melt granulation involves melting the carrier and dissolving the active pharmaceutical ingredient in the resulting melt. The melt can be granulated with a diluent such as microcrystalline cellulose, then blended with other excipients and filled into capsules or compressed into tablets. Similarly, hot melt extrusion involves melting the carrier and dissolving the active pharmaceutical ingredient in the resulting melt, followed by blending and extrusion.

The final dosage forms comprising the powdered, free-flowing compositions can be provided in the form of a capsule, a tablet, an implant, a troche, a lozenge, a temporary or permanent suspension, an ovule, a suppository, a wafer, a chewable tablet, a quick or fast dissolving tablet, an effervescent tablet, a buccal or sublingual solid, a granule, a film, a sprinkle, a pellet, a bead, a pill, a powder, a triturate, a platelet, a strip or a sachet. Compositions can also be administered as a "dry powder," where the finished dosage form is placed directly on the tongue and swallowed or followed with a drink or beverage. These forms are well known in the art and are packaged appropriately. The compositions can be formulated for oral, nasal, buccal, ocular, urethral, transmucosal, vaginal, topical or rectal delivery, although oral delivery is presently preferred.

The final dosage forms can be coated with one or more enteric coatings, seal coatings, film coatings, barrier coatings, compress coatings, fast disintegrating coatings, or enzyme degradable coatings. Multiple coatings can be applied for desired performance. Further, the final dosage forms can be designed for immediate release, pulsatile release, controlled release, extended release, delayed release, targeted release, synchronized release, or targeted delayed release. For release/absorption control, the release profile can be effected by a polymeric matrix composition, a coated matrix composition, a multiparticulate composition, a coated multiparticulate composition, an ion-exchange resin-based composition, an osmosis-based composition, or a biodegradable polymeric composition.

A pharmaceutical composition can include an oil-free solid dispersion including a water-insoluble active pharmaceutical ingredient and a carrier.

The composition can be a solid dispersion. In other words, the dispersion can be a molecularly unilamellar mixture of chemically distinct compounds in the solid state, as opposed to, e.g., a colloidal dispersion, emulsion, or solution. The solid dispersion is also distinct from a physical mixture. In a physical mixture, two or more solid components are combined and become intermingled but do not interact substantially at the chemical level. Individual particles in a physical mixture are substantially composed of the compounds present in one of the starting materials. In a solid dispersion, however, individual particles are composed of compounds present in different starting materials. A physical mixture can be made, for example, by combining two (or more) different solid ingredients in a vessel and mixing the two solids. A solid dispersion can be made, for example, by dissolving two (or more) different solid ingredients in a common solvent, and then removing the solvent (e.g., by evaporation). The solid dispersion can be a solid solution.

The solid dispersion can be oil-free. In other words, the solid dispersion can be free of hydrophobic materials that are liquid at physiologically relevant temperatures (e.g., in the range of 0° C. to 40° C.; 4° C. to 37° C.; 10° C. to 30° C., or 15° C. to 25° C.; or, for example, room temperature). The carrier itself may be a hydrophobic liquid when in its pure state. The solid dispersion, however, is free of other oils. The carrier can account for a large fraction of the material in the solid dispersion. The carrier can account for a greater fraction of the material in the solid dispersion than any other ingredient. For example, the solid dispersion can include at least 40% by weight, at least 50% by weight, at least 60% by weight, at least 70% by weight, at least 80% by weight, or at least 90% by weight of the carrier.

The carrier can be water-insoluble; for example, the carrier can be a water-insoluble matrix forming material. In general, a water-insoluble carrier can be preferable in formulations involving a water-insoluble active pharmaceutical ingredient.

The carrier can be water-dispersable. In other words, the carrier can become dispersed in an aqueous medium, e.g., as a colloid. In some circumstances, when a suitable surfactant and water-immiscible solvent are present, the carrier, solvent and surfactant act together to provide an emulsion (e.g., an oil-in-water emulsion). However, formation of an emulsion is not always preferable; in some circumstances, the carrier can disperse in an aqueous medium without the aid of additional components. Water dispersability of the carrier can be important for ensuring that the active pharmaceutical ingredient is bioavailable.

The carrier can be enzymatically degradable. Once dispersed in the aqueous medium, the carrier is degraded so as to free the active pharmaceutical ingredient from the carrier. Enzymatic degradation is desirable because it occurs only in the desired physiological medium, i.e., in the subject.

The relative amounts of active pharmaceutical ingredient to carrier in the solid dispersion can be in the range of 1:1000 to 2:1, such as in the range 1:20 to 1:1, or in the range 1:9 to 1:2.

Pharmaceutical compositions include lixivaptan, or pharmaceutically acceptable derivatives thereof. Lixivaptan is also known by other names, including 5-fluoro-2-methyl-N-[4-(5H-pyrrolo[2,1-c]-[1,4]-benzodiazepin-10(11H)-ylcarbonyl)-3-chlorophenyl]benzamide, and VPA-985.

Lixivaptan is very poorly soluble in water (less than 20 ng/mL). Salt formation (a frequently used approach to increase aqueous solubility) was not possible. The bioavailability of lixivaptan can be extremely low in conventional dosage forms (i.e., when blended with excipients and compressed into tablets or filled into capsules).

Bioavailable formulations were prepared by dissolving lixivaptan in liquid or semi-solid vehicles that incorporate large quantities of polyethylene glycol (PEG). However, PEG-based formulations are highly hygroscopic (especially in the case of lower molecular weight PEGs, such as, for example, PEG 400 or PEG 1000). When moisture is absorbed into the formulation, it triggers lixivaptan crystallization. Crystalline lixivaptan has poor bioavailability. Moisture can also increase the chemical degradation of lixivaptan. In order to provide an acceptable shelf life, the PEG-based formulation therefore requires protection from moisture by packaging into foil or foil blisters and/or using desiccants. Moreover, PEG contains small amounts of reactive peroxides as impurities. These impurities can cause considerable degradation of lixivaptan in this dosage form. The degradation caused by the impurities can be mitigated by including anti-oxidants, so as to maintain acceptable chemical stability.

A lixivaptan formulation based on a vitamin E semi-ester (e.g., vitamin E succinate, VES, or alpha-tocopherol succinate, ATS) provides a surprisingly highly bioavailablity for lixivaptan. For example, the bioavailability can be more than 3 times higher than the PEG-based formulation. It is non-hygroscopic and uses inert excipients without increasing the active pharmaceutical ingredient degradation. A VES-based formulation provides good chemical stability even without the use of anti-oxidants. In addition, the formulation has excellent physical stability (no crystallization of the active observed) even when exposed to accelerated stability conditions. A VES-based formulation can be substantially free of the original crystalline form of lixivaptan when it contains less than 25%, less than 15%, less than 10%, less than 5%, less than 3%, less than 1%, less than 0.5% or less than 0.1% crystalline lixivaptan as determined by suitable methods, such as, for example, differential scanning calorimetry (DSC) or X-ray powder diffraction (XRPD).

Unexpectedly, the bioavailability of lixivaptan in the VES formulation is much higher than what would be predicted from in vitro dissolution alone. The PEG-based formulation has similar or even slightly better in vitro dissolution properties than the VES-based formulation, but VES formulation F-130 (see below) had bioavailability that is 3 times that of the PEG-based formulation.

Surprisingly, the VES formulation has rapid dissolution properties even though the individual components are not readily soluble in aqueous solutions (lixivaptan is very poorly soluble, and VES is also water-insoluble).

VES is crystalline and can maintain crystallinity in the formulation. Therefore, the formulation is a crystalline matrix and lixivaptan is dispersed or dissolved within the VES crystals. The VES matrix prevents agglomeration of lixivaptan molecules, restricting the crystallinity of lixivaptan in the solid dispersion. In contrast, most amorphous dispersions of active pharmaceutical ingredients use amorphous polymers to dissolve the active and keep it amorphous.

A non-polymer-based crystalline matrix (such as that provided by VES) can be non-hygroscopic. In the case of lixivaptan, a non-hygroscopic carrier can help increase chemical stability of the drug.

Desirably, the lixivaptan and VES formulation can be free-flowing and can be easily formulated into a tablet.

Including zein in a lixivaptan-VES formulation can facilitate spray drying in conventional spray drying equipment. In the absence of any anti-tacking agents, a solution including VES and lixivaptan solution can be tacky and difficult to spray dry. Particulate anti-tacking agents such as colloidal silicon dioxide and talc can be used in fluid bed spray-granulation or fluid bed drug layering processes; however, these agents are generally incompatible with spray drying. Zein dissolves in acetone at high concentration and can be incorporated in the solution including both VES and lixivaptan. A solution including VES, zein, and lixivaptan is generally non-tacky and can be spray dried easily. When spray dried, a dry, free flowing powder that is generally easily formulated results.

The lixivaptan-VES formulation can further include additional ingredients, such as: fillers or diluents such as sugars (e.g., lactose, mannitol), microcrystalline cellulose, modified starch, dicalcium phosphate, or dextrins; binders such as povidone, methylcellulose, hypromellose, starch, gelatin, or PEG; disintegrants such as crospovidone, sodium croscarmellose, sodium starch glycolate, starch, or pregelatinized starch; anti-adherents (anti-tacking agents) such as talc, colloidal silicon dioxide, polyethylene glycol (PEG) 3350, PEG 6000, or PEG 8000; anti-oxidants such as ascorbic acid, butylated hydroxyanisole, butylated hydroxytoluene, or propyl gallate; glidants such as colloidal silicon dioxide; and surfactants such as poloxamers, polysorbate 80, or sodium lauryl sulfate (SLS).

Manufacturing the lixivaptan-VES formulation includes dissolving the active pharmaceutical ingredient and a carrier in a common solvent and then evaporating the solvent. This process results in incorporating the active in the carrier matrix.

When the active pharmaceutical ingredient is incorporated in the carrier, the active pharmaceutical ingredient is prevented from crystallizing. If the carrier is crystalline in a pure state, it largely maintains a crystalline structure in the solid dispersion. If the carrier is amorphous in a pure state, it largely maintains its amorphous character in the solid dispersion.

The solvent can be, for example, acetone, methanol, ethanol, methyl ethyl ketone, ethyl acetate, toluene, methylene chloride, chloroform, DMSO, pentane, hexane, or other solvents, or a combination thereof. In some cases, it is desirable to use an anhydrous solvent, i.e., a solvent that has been treated and maintained under conditions that ensure the solvent is rigorously free of water. In some cases, the presence of small amounts of water (such as amounts that result from exposure of the solvent to air) can be tolerated. In other cases, it may be desirable to include an amount of water in the solvent. The solvent is chosen for its ability to simultaneously dissolve both the active pharmaceutical ingredient and the carrier at the desired concentrations.

The solvent is removed by evaporation. In some cases it can be desirable to facilitate rapid evaporation, e.g., by heating, vacuum evaporation, spray-drying, or a fluid-bed process (fluid bed granulation or fluid bed layering). Preferably, the evaporation process is one that is a conventional and scalable pharmaceutical process and is commonly used in cGMP production of pharmaceuticals.

In a fluid bed granulation manufacturing process, the active pharmaceutical ingredient and carrier solution is sprayed onto inert pharmaceutical excipients (fillers or diluents) to produce a granulation. The granulation later is compressed into tablets or filled into capsules. A commonly used anti-adherent (anti-tacking agent) such as talc or colloidal silicone dioxide can be suspended in the solution to overcome any undesirable tackiness of the solution. Alternatively, a drug-layering process that involves spraying the active pharmaceutical ingredient and carrier solution with an added anti-adherant onto small inert beads (e.g., sugar spheres or microcrystalline cellulose spheres) can be used to produce drug pellets or beads. Those beads can then be coated with a moisture protective film, if needed, and filled into capsules, or they can be compressed into tablets after blending with additional excipients.

The composition can include a secondary carrier material. The secondary carrier material is chosen to provide desirable properties that complement the properties of the primary carrier. (In this context, "primary carrier" and "secondary carrier" indicate the relative amounts of the material, by weight, in the composition.) For example, if the primary provides good dissolution of the active pharmaceutical ingredient, but less than ideal drying properties, then the secondary carrier is chosen so as to improve the drying properties of the solid composition.

Materials useful as secondary carriers include, for example, zein, casein, whey, collagen, gelatin, insoluble amino acid, protein hydrolysates, or combinations thereof. Zein is soluble in acetone and it has anti-tacking properties that are desirable for spray-drying a solution of active pharmaceutical ingredient and a primary carrier. The resulting material is a free flowing dry powder that can be compressed into tablets or filled into capsules after blending with other ingredients. A dry granulation method such as roller compaction can be used to increase the bulk density of the powder prior to tablet compression or capsule filling.

Example 1

Formulation F-130

Formulation F-130 is a VES-based solid dispersion of lixivaptan. F-130 is prepared in two stages. The first stage involves forming a solid dispersion or solid solution of VES and lixivaptan (F-126). In the second stage, the F-126 solid is combined with other excipients and loaded into capsules. The following table describes the relative amounts of materials in F-126 and F-130.

| Component | F-126 (Intermediate) | F-130 (Capsule) |
|---|---|---|
| Lixivaptan | 10.4 | / |
| VES | 89.6 | / |
| F-126 | / | 96 |
| Polyplasdone ® XL-10 | / | 3 |
| SDS | / | 1 |
| Total | 100 | 100 |

Example 2

Preparation of F-126C

To prepare coarse particles of F-126 (F-126C), the tare weight of a 1 L round bottom flask was recorded. A 10 g portion of lixivaptan and an 86 g portion of VES were added to the flask. Next, 400 mL acetone was added and stirred at 50° C. to obtain a clear solution. The solution was passed through a 0.8 µm filter membrane. The flask was rinsed with an extra 100 mL of acetone, which was combined with the filtrate. The acetone was removed by rotary evaporation until the residual solvent was less than 3%. The mixture was incubated at −30° C. overnight to solidify. The resulting solid was broken into small pieces and plenary-milled to reduce size sufficiently to pass through a 60 mesh sieve. The solid was oven dried at 40° C. until residual solvent was less than 0.5% (as determined by thermogravimetric analysis (TGA)) to obtain F-126C.

Example 3

Preparation of F-130C

F-130C was prepared by combining 3.84 g of F-126, 0.04 g SDS and 0.12 g of Crospovidone XL-10. These were mixed by rotation at 20 rpm for 30 minutes.

Example 4

Micronized F-126 (F-126M)

F-126C (9.6 g) and SDS (0.1 g) were combined and mixed well. The mixture was treated by Jet-Mill until the particle size was less than 100 µm.

Example 5

Preparation of F-130M

F-126M (3.88 g) and Crospovidone XL-10 (0.12 g) were combined and mixed well by rotation at 20 RPM for 30 min. The table below summarizes physical properties of some formulations.

| | F-126C | F-126M | F-130C | F-130M |
|---|---|---|---|---|
| Bulk density (g/cm$^3$) | 0.38 | 0.11 | n.d. | n.d. |
| Particle size (µm) | $D_{(v, 10)} = 36.6$ | $D_{(v, 10)} = 8.6$ | n.d. | n.d. |
| | $D_{(v, 50)} = 121.8$ | $D_{(v, 50)} = 26.0$ | | |
| | $D_{(v, 90)} = 267.0$ | $D_{(v, 90)} = 75.9$ | | |
| lixivaptan Assay (%, in powder) | 9.48 | n.d. | 9.51 | 9.56 |
| lixivaptan Purity (%) | 99.6 | n.d. | 99.6 | 99.6 |

Example 6

Stability

Figure 1B:
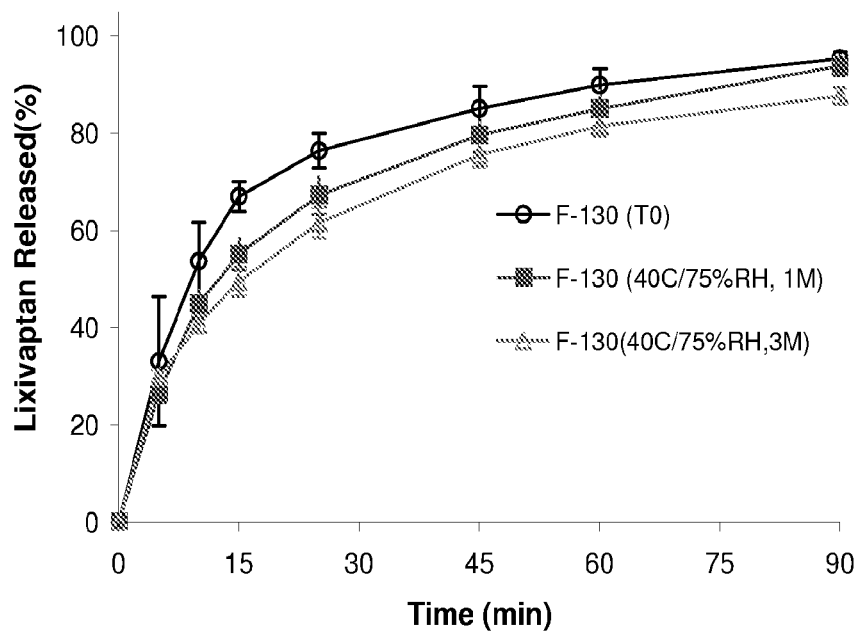

The solid lixivaptan formulation was loaded in hard gelatin capsules (CapsuGel 00CS) by weight to provide 50 mg lixivaptan per capsule. The following table describes the purity (determined by chromatography) of lixivaptan in F-130 at time zero ($T_0$) and under different storage conditions. The dissolution profiles of these samples were also measured (FIGS. 1A and 1B).

| Sample ID | Lixivaptan (%) |
|---|---|
| $T_0$ | 99.7 |
| 25° C./60% RH/1M | 99.5 |
| 25° C./60% RH/3M | 99.3 |
| 40° C./75% RH/1M | 98.9 |
| 40° C./75% RH/3M | 98.2 |

Example 7

Pharmacokinetics

The following table presents results of pharmacokinetic tests in monkeys.

| Formulation | | HL ((h) | Tmax (h) | Cmax (ng/mL) | AUC24 (h * ng/mL) | Tlag (h) |
|---|---|---|---|---|---|---|
| PEG-based | N | 3 | 3 | 3 | 3 | 3 |
| capsule | Mean | 3.24 | 2.00 | 238 | 1200 | 0 |
| (Reference) | SD | 2.52 | 0.00 | 73.9 | 324 (cv = 27%) | NA |
| F-130 (VES) | N | 3 | 3 | 3 | 3 | 3 |
| | Mean | 3.79 | 4.00 | 638 | 3850 | 0.5-1.0 |
| | SD | 0.29 | 0.00 | 363 | 526 (cv = 14%) | TBD |

Example 8

Physical Properties of Lixivaptan Formulations

FIG. 2 displays X-ray powder diffraction spectra for samples of lixivaptan, F-126, and three different preparations of F-130 (denoted F-130-a, F-130-b, and F-130-c).

FIG. 3A present thermogravimetric analysis (TGA) and differential scanning calorimetry (DSC) results for a sample of F-130 aged 6 months at 40° C. TGA showed a weight loss of 1.15% at 120° C., corresponding to water evaporation. DSC showed evidence of a crystalline matrix without the melting endotherm of lixivaptan.

FIG. 3B present TGA and DSC results for a sample of F-130 aged 6 months at 25° C. TGA showed a weight loss of 1.24% at 120° C., corresponding to water evaporation. DSC showed evidence of a crystalline matrix without the melting endotherm of lixivaptan.

Example 9

Additional Formulations

The table below describes the composition of additional formulations:

| Components | Composition (%, w/w) | | | | | | |
|---|---|---|---|---|---|---|---|
| | F-126 | F-130 | F-150 | F-152 | F-168 | F-307 | F-314 |
| Lixivaptan | 10.4 | / | / | / | / | 10 | / |
| Vitamin E Succinate (VES), USP | 89.6 | / | / | / | / | 60 | / |
| Zein, FC | / | / | / | / | / | 30 | / |
| F-126 | / | 96 | 96 | 96 | 93.2 | / | / |
| F-307 | / | / | / | / | / | / | 94.3 |
| Sodium lauryl sulfate (SDS), NF | / | 1 | 1 | 1 | 0.97 | / | 0.9 |
| Cab-O-Sil | / | / | / | / | 0.97 | / | / |
| Polyplasdone ® XL-10, NF | / | 3 | / | / | / | / | / |
| Ac-Di-Sol, NF | / | / | 3 | / | 4.85 | / | / |
| Explore-Tab, NF | / | / | / | 3 | / | / | 4.7 |

To prepare F-130, F-150 and F-152, 3.88 g of F-126C and 0.12 g disintegrant (Polyplasdone® XL-10, Ac-Di-Sol, Explore-Tab, for F-130, F-150 and F-152, respectively) were combined and mixed well.

To prepare F-168, 1.88 g F-126M, 0.019 g Cab-O-Sil and 0.097 g Ac-Di-Sol were combined and mixed well.

To prepare F-307, to 1 g of lixivaptan in a 250 mL glass bottle was added 120 mL of 75% acetone in water. The material was heated at about 60° C. until complete dissolution. To this solution, 6 g of VES and 3 g of zein were added and the solution mixed until complete dissolution was observed.

The solution was subjected to spray drying under the following conditions: solution temperature, 55-60° C.; feed rate, 4-5 mL/min; drying airflow rate, 0.3-0.4 m3/min; inlet air temperature, 120° C.; outlet air temperature, 75-80° C. The spray dried powder was transferred to a tray and dried in a vacuum oven at 50° C. until the residual solvent was less than 2% by weight (determined by TGA). The solid was passed through a 70 mesh sieve to obtain F-307.

To prepare F-314, F-307, SDS, and Ac-Di-Sol were combined in the appropriate ratio and mixed well.

Figure 4:
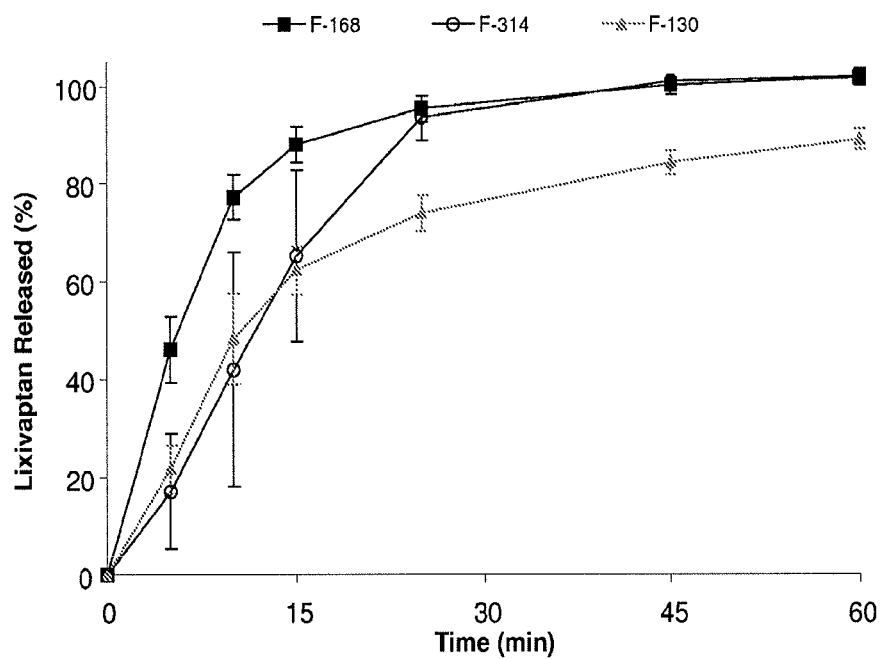
FIG. 4 presents dissolution profiles of lixivaptan formulations.

FIG. 4 compares the dissolution time profiles for the 00CS capsules filled with either F-130, F-168, or F-314.

Example 10

Formulations F-315 and F-316

The table below describes the composition of additional formulations:

| Preparation of F-315 and F-316 | | |
|---|---|---|
| % w/w | F-315 (Intermediate) | F-316 |
| Lixivaptan | 11.6 | 11.0 |
| VES | 56.8 | 54.0 |
| Zein | 31.6 | 30.0 |
| SDS | / | 1.0 |
| Cab-O-Sil | / | 0.0 |
| Ac-Di-Sol | / | 4.0 |
| Total | 100 | 100 |

A batch of 60 g F-315 was prepared using a spray-dryer. The spray-dried product was further dried in oven at 40-50° C. to less than 2% solvent residue. The powder was passed thru 70-mesh sieve and mixed well with SDS and Ac-Di-Sol to obtain a F-316 powder blend.

Figure 5:
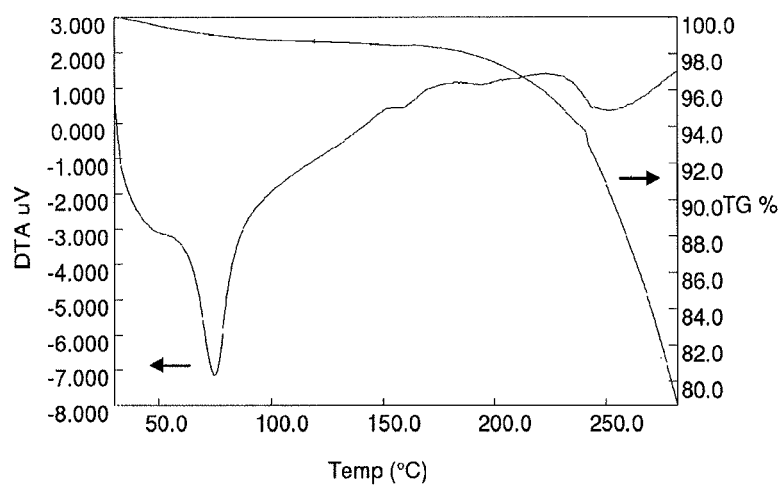
FIG. 5 shows TGA and DSC results for a lixivaptan formulation.

FIG. 5 shows TGA and DSC results for F-315.

Example 11

Antioxidants

The table below describes several formulations tested under accelerated ageing conditions (60° C., ambient RH, open to air for 60 hours) to test the effect of including antioxidants on the stability of lixivaptan.

| % w/w | T-1* | T-2 | T-3 | T-4 | T-5 |
|---|---|---|---|---|---|
| Lixivaptan | 10.40 | 10.34 | 10.29 | 10.38 | 10.29 |
| VES | 89.60 | 89.37 | 88.75 | 89.56 | 88.43 |
| Butylated hydroxyanisole (BHA) | / | 0.26 | 0.86 | / | / |
| Butylated hydroxytoluene (BHT) | / | 0.02 | 0.09 | / | / |
| Alpha tocopherol | / | / | / | 0.05 | 0.05 |
| Ascorbyl palmitate | / | / | / | / | 1.23 |
| Total | 100 | 100 | 100 | 100 | 100 |

*T-1: F-126

Including 0.26% BHA and 0.02% BHT (formulation T-2) showed increased lixivaptan stability in F-126 under the conditions used.

| Sample | T-1 | T-2 | T-3 | T-4 | T-5 |
|---|---|---|---|---|---|
| Initial | 10.26 | 10.07 | 9.95 | 10.18 | 9.76 |
| 60° C., 60 h | 9.97 | 10.00 | 9.19 | 9.94 | 9.20 |
| Assay recovery over initial (%) | 97.1 | 99.3 | 92.3 | 97.7 | 94.3 |

Example 12

Zein-Containing Formulations

The table below describes the composition of a series of zein-containing formulations of lixivaptan.

| Component (%, w/w solid) | F-128 | F-304 | F-305 | F-306 | F-307 | F-308 | F-309 |
|---|---|---|---|---|---|---|---|
| Lixivaptan | 20 | 10 | 10 | 10 | 10 | 10 | 10 |
| Zein | 80 | 75 | 60 | 45 | 30 | 15 | 45 |
| VES | / | 15 | 30 | 45 | 60 | 75 | / |
| PL90H | / | / | / | / | / | / | 45 |

These formulations were prepared by weighing out 1 g lixivaptan into a 250 mL glass bottle. Between 100 mL and 120 mL of 75% acetone in water was added and heated at about 60° C. to dissolve all. Zein and VES were added to the solution in the appropriate amounts and mixed well. The solution was spray dried using the following conditions: Solution temperature, 55-60° C.; feed rate, 4-5 mL/min; drying airflow rate, 0.3-0.4 m3/min; inlet air temperature, 120° C.; outlet air temperature, 75-80° C.

The spray dried powder was transferred to a tray, and dried in a vacuum oven at 50° C. until the residual solvent content was less than 4% by weight as determined by TGA. The resulting solid was passed through a 70-mesh sieve.

| For-mulation | spray drying feasible? | Powder density (g/mL) | Flowability | Solubility (mg/mL in 1.5% SDS, 25° C.) 1 h | 24 h | Solvent residue (%, 120° C.) |
|---|---|---|---|---|---|---|
| lixivaptan | — | — | — | 0.019 | 0.024 | — |
| F-128 | Yes | 0.101 | Poor, fluffy | 0.30 | 0.89 | 3.7 |
| F-304 | Yes | 0.159 | Poor, fluffy | 0.34 | 1.05 | 3.4 |
| F-305 | Yes | 0.122 | Fair | 0.33 | 0.19 | 3.4 |
| F-306 | Yes | 0.134 | Acceptable | 0.26 | 1.05 | 2.3 |
| F-307 | Yes. After further oven dry | 0.170 | Good | 0.93 | 1.19 | 1.8 |
| F-308 | No. Obtained sticky viscous liquid | nd | nd | nd | nd | nd |
| F-309 | No. No solvent was found to dissolve all materials | nd | nd | nd | nd | nd |

Figure 6:
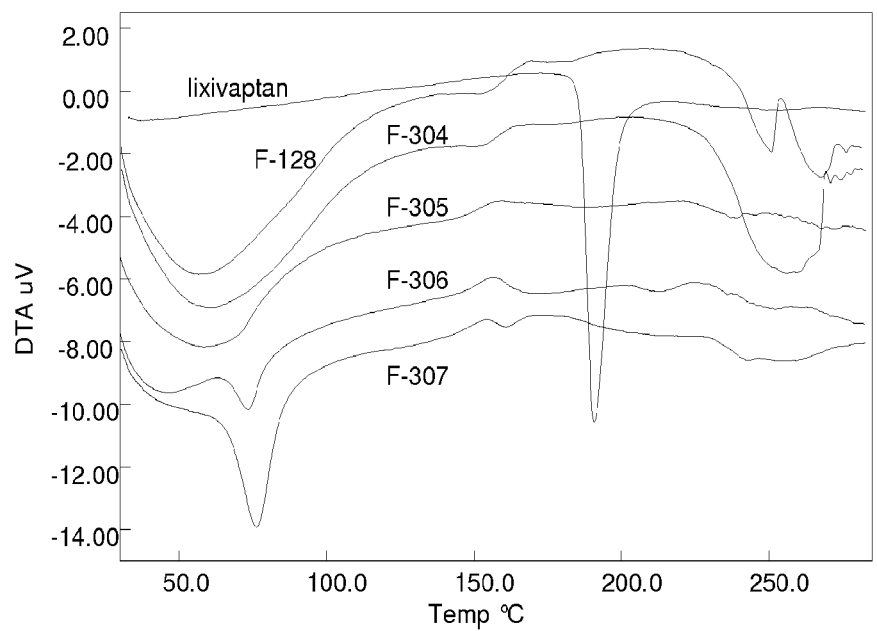
FIG. 6 shows DTA results for lixivaptan and lixivaptan formulations.

FIG. 6 shows differential thermal analysis (DTA) results for lixivaptan, F-128, F-304, F-305, F-306 and F-307. For zein concentrations of 60% or more, the DTA peak associated with VES (at about 80° C.) was not observed. Three compositions (F-305, F-306 and F-307) were successfully prepared by spray draying. These compositions were also free of crystalline lixivaptan, as determined by DSC, and provided suitable levels of solubility for lixivaptan.

| Compounding table (mg per vessel containing 450 mL) | | | | | | |
|---|---|---|---|---|---|---|
| Components | F-139* | F-310** | F-311*** | F-312*** | F-313*** | F-314**** |
| F-128 | 125 | 125 | / | / | / | / |
| F-304 | / | / | 250 | / | / | / |
| F-305 | / | / | / | 250 | / | / |
| F-306 | / | / | / | / | 250 | / |
| F-307 | / | / | / | / | / | 250 |
| Cab-O-Sil | 1.32 | 1.32 | 2.5 | 2.5 | 2.5 | / |
| SDS | 1.32 | 1.32 | 2.5 | 2.5 | 2.5 | 2.5 |
| Crospovidone XL-10 | 3.95 | / | / | / | / | / |
| Ac-Di-Sol | / | 6.58 | 12.5 | 12.5 | 12.5 | 12.5 |
| Avicel PH101 | / | 78.9 | / | / | / | / |
| Total | 131.6 | 213.2 | 267.5 | 267.5 | 267.5 | 265.0 |
| Lixivaptan/vessel (mg) | 25 | 25 | 25 | 25 | 25 | 25 |
| # of 00CS/vessel | 2 | 2 | 2 | 2 | 2 | 2 |

*control
**Add 3% Ac-Di-Sol and 35% MCC extragranularly. 37% MCC is the max allowed by vol.
***Add 5% Ac-Di-Sol extragranularly.
****No Cab-O-Sil needed for flow.

| Composition (% wt) | | | | | | |
|---|---|---|---|---|---|---|
| Components | F-139 | F-310 | F-311 | F-312 | F-313 | F-314 |
| Lixi | 19 | 11.7 | 9.3 | 9.3 | 9.3 | 9.4 |
| Zein | 78 | 46.9 | 70.1 | 56.1 | 42.1 | 28.3 |
| VES | / | / | 14.0 | 28.0 | 42.1 | 56.6 |
| Cab-O-Sil | 1 | 0.6 | 0.9 | 0.9 | 0.9 | / |
| SDS | 1 | 0.6 | 0.9 | 0.9 | 0.9 | 0.9 |
| Crospovidone XL-10 | 3 | / | / | / | / | / |
| Ac-Di-Sol | / | 3.1 | 4.7 | 4.7 | 4.7 | 4.7 |
| Avicel PH101 | / | 37.0 | / | / | / | / |
| Total | 100 | 100 | 100 | 100 | 100 | 100 |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

Other embodiments are set forth within the following claims.

What is claimed is:

1. A pharmaceutical composition comprising a single oral dosage form including an oil-free and substantially water-free solid dispersion, the dispersion including a therapeutically effective amount of lixivaptan and 50% or more by weight of a vitamin E semi-ester.

2. The composition of claim 1, wherein the dispersion further includes a surfactant.

3. The composition of claim 2, wherein the surfactant is an alkyl sulfate salt.

4. The composition of claim 3, wherein the alkyl sulfate salt is sodium lauryl sulfate.

5. The composition of claim 1, wherein the dispersion is substantially free of crystalline lixivaptan.

6. The composition of claim 1, wherein the dispersion includes 60% or more by weight of vitamin E semi-ester.

7. The composition of claim 1 further including a disintegrant.

8. The composition of claim 7, wherein the disintegrant is a crosslinked poly(vinylpyrrolidone).

9. The composition of claim 1, wherein the dispersion further includes a water soluble polymer.

10. The composition of claim 1, the dispersion further includes a plant protein.

11. The composition of claim 10, wherein the plant protein is zein.

12. The composition of claim 1 further including a surfactant.

13. The composition of claim 12, wherein the surfactant is an alkyl sulfate salt.

14. The composition of claim 13, wherein the alkyl sulfate salt is sodium lauryl sulfate.

15. The composition of claim 1, wherein the vitamin E semi-ester is alpha-tocopheryl succinate.

16. A method of making a pharmaceutical composition comprising:

dissolving an amount of lixivaptan in a non-aqueous solvent;

dissolving an amount of a vitamin E semi-ester derivative in the non-aqueous solvent; and removing the solvent, thereby forming a solid dispersion including lixivaptan and the vitamin E semi-ester derivative.

17. The method of claim 16, wherein the vitamin E semi-ester derivative is alphatocopheryl succinate.

18. The method of claim 16, further comprising mixing the solid dispersion with a disintegrant.

19. The method of claim 18, further comprising mixing the solid dispersion with a surfactant.

20. The method of claim 16, further comprising dissolving an amount of a water-soluble protein in the non-aqueous solvent.

21. The method of claim 20, wherein removing the solvent includes spray drying.

22. The method of claim 16, wherein the dispersion is substantially free of crystalline lixivaptan.

* * * * *

UNITED STATES PATENT AND TRADEMARK OFFICE
CERTIFICATE OF CORRECTION

PATENT NO.        : 8,877,746 B2                                        Page 1 of 1
APPLICATION NO.   : 13/391440
DATED             : November 4, 2014
INVENTOR(S)       : Chen et al.

It is certified that error appears in the above-identified patent and that said Letters Patent is hereby corrected as shown below:

Title page, item (73) Assignee:

Replace "Cardioklne, Inc." with --Cardiokine, Inc.--

Signed and Sealed this
Fourteenth Day of April, 2015

Michelle K. Lee
*Director of the United States Patent and Trademark Office*